United States Patent
Oftring et al.

(10) Patent No.: US 8,455,682 B2
(45) Date of Patent: Jun. 4, 2013

(54) METHOD FOR THE PRODUCTION OF AMINODICARBOXYLIC ACID-N,N-DIACETIC ACIDS

(75) Inventors: Alfred Oftring, Bad Duerkheim (DE); Armin Stamm, Nieder-Olm (DE); Friedrich Wirsing, Kaiserslautern (DE); Gerold Braun, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 129 days.

(21) Appl. No.: 12/919,149

(22) PCT Filed: Mar. 2, 2009

(86) PCT No.: PCT/EP2009/052447
§ 371 (c)(1), (2), (4) Date: Aug. 24, 2010

(87) PCT Pub. No.: WO2009/109544
PCT Pub. Date: Sep. 11, 2009

(65) Prior Publication Data
US 2011/0004016 A1 Jan. 6, 2011

(30) Foreign Application Priority Data
Mar. 3, 2008 (EP) .................... 08152207

(51) Int. Cl.
*C07C 229/16* (2006.01)
(52) U.S. Cl.
USPC .......................................... 562/571
(58) Field of Classification Search
CPC .................................... C07C 227/26
See application file for complete search history.

(56) References Cited

U.S. PATENT DOCUMENTS

| 2,500,019 A | 3/1950 | Berswroth |
| 5,948,748 A | 9/1999 | Hagino et al. |
| 2010/0324334 A1* | 12/2010 | Boonstra et al. ............. 562/554 |

FOREIGN PATENT DOCUMENTS

| DE | 2 339 888 | | 2/1974 |
| DE | 42 11 713 | | 10/1993 |
| DE | 4211713 | A1 * | 10/1993 |
| EP | 0 884 381 | | 12/1998 |
| WO | 2009 024518 | | 2/2009 |

OTHER PUBLICATIONS

U.S. Appl. No. 13/030,816, filed Feb. 18, 2011, Baumann, et al.
International Search Report issued Jul. 7, 2009 in PCT/EP09/052447 filed Mar. 2, 2009.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

Provided is a method for the production of aminodicarboxylic acid N,N-diacetic acids of formula (I),

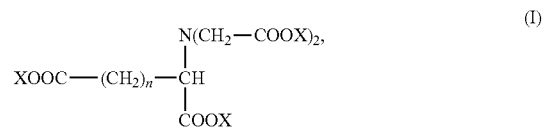

wherein X is independently hydrogen or an alkali metal and n is 1 or 2. Aminodicarboxylic acid-N,N-diacetic acids of high purity can be yielded. The method involves: a) reacting an aminodicarboxylic acid, with 0.8 to 1.2 mole equivalents of formaldehyde and with 0.8 to 1.2 mole equivalents of hydrocyanic acid; b) reacting the reaction products of a) with 0.8 to 1.2 mole equivalents of hydrocyanic acid and with 0.8 to 1.2 mole equivalents of formaldehyde; c) hydrolyzing in the reaction product obtained in b).

18 Claims, No Drawings

METHOD FOR THE PRODUCTION OF AMINODICARBOXYLIC ACID-N,N-DIACETIC ACIDS

CROSS REFERENCE TO RELATED APPLICATIONS

The present application is the national stage of international application PCT/EP2009/052447, filed on Mar. 2, 2009, and claims the benefit of the filing date of European Application No. 08152207.0, filed on Mar. 3, 2008.

DESCRIPTION

The present invention relates to a process for preparing aminodicarboxylic acid-N,N-diacetic acids of the general formula I

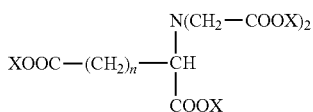

in which X is independently hydrogen or alkali metal and n is 1 or 2. The invention further relates to aminodicarboxylic acid-N,N-diacetic acids of high purity.

Aminodicarboxylic acid-N,N-diacetic acids I are of interest in particular as complexing agents in washing and cleaning compositions. The substances customary for these purposes, such as polycarboxylates, phosphonates, triphosphates, ethylenediaminetetraacetic acid (EDTA) and nitrilotriacetic acid (NTA) are afflicted with disadvantages. More particularly, they contribute to eutrophication, have poor biodegradability or have toxic effects. An alternative is constituted by the inexpensive and biodegradable glutamic acid-N,N-diacetic acid (GLDA) and salts thereof, which are of the formula I where n=2.

Processes for preparing the N,N-diacetic acid derivatives of α-amino acids have been known in principle for some time. For instance, US 2500019 describes the preparation of such diacetic acid derivatives by reaction of α-amino acids with formaldehyde and sodium cyanide, preferably in strongly basic aqueous solution at temperatures of from 30 to 100° C. With glutamic acid as the α-amino acid, a mixture of glutamic acid-N,N-diacetic acid and α-aminobutyric acid-N,N-diacetic acid was obtained, since the terminal carboxyl group was partly decarboxylated under the strongly basic conditions.

DE 4211713 describes processes for preparing aminodicarboxylic acid-N,N-diacetic acids based on acidic and basic Strecker reactions. In this case, the α-amino acid is reacted with at least 2 mol of formaldehyde and at least 2 mol of hydrocyanic acid or alkali metal cyanide. The comparatively low yield of 91% based on aspartic acid leads to the suspicion that undesired by-products, for instance NTA, have formed, which are difficult to remove.

It is thus an object of the present invention to provide a simple-to-perform process for preparing aminodicarboxylic acid-N,N-diacetic acids of the general formula I designated above, which affords these compounds in good yields with low by-product fractions. More particularly, the proportion of NTA should be at a minimum. It is a further object of the present invention to provide such aminodicarboxylic acid-N,N-diacetic acids of high purity.

These and further objects are achieved by the process described in detail hereinafter.

The present invention provides a process for preparing aminodicarboxylic acid-N,N-diacetic acids of the general formula I designated above comprising the following steps:

a) reacting an aminodicarboxylic acid of the general formula II

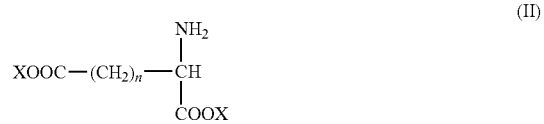

in which X and n are each as defined above with from 0.8 to 1.2 molar equivalents of formaldehyde and with from 0.8 to 1.2 molar equivalents of hydrocyanic acid;

b) reacting the reaction product obtained in step a) with from 0.8 to 1.2 molar equivalents of hydrocyanic acid and with from 0.8 to 1.2 molar equivalents of formaldehyde;

c) hydrolyzing the reaction product obtained in step b).

The process according to the invention is associated with a series of advantages. Firstly, it is comparatively simple to perform, for example, in a one-pot synthesis with short cycle times. In addition, it affords the desired aminodicarboxylic acid-N,N-diacetic acids in good yields and high purity, and so complicated purification processes are not necessary. The process can also be handled efficiently on the industrial scale.

In the process according to the invention, formaldehyde is understood to mean the formaldehyde reactant, either in the gaseous state or dissolved in an aqueous solvent, preferably in a concentration of from 20 to 50% by weight, or formaldehyde equivalents. Such equivalents are compounds which release formaldehyde in the course of the reaction or are converted directly to the same products such as formaldehyde. Examples of such equivalents known to the person skilled in the art are paraformaldehyde, trioxane and methylal, and also mixtures thereof or mixtures with formaldehyde. Preference is given to using an aqueous solution of formaldehyde.

In the process according to the invention, the hydrocyanic acid reactant is used either in aqueous solution or preferably in pure form.

In step a) of the process according to the invention, the free aminodicarboxylic acid II or the partly or fully neutralized aminodicarboxylic acid II is used, a neutralization being effected preferably with alkali metal bases such as sodium hydroxide, potassium hydroxide, sodium carbonate, potassium carbonate, sodium hydrogencarbonate or potassium hydrogencarbonate. It is also possible to use mono- or dialkali metal salts of II or mixtures thereof, preference being given to the sodium salts. Based on the compound II used, in general, in accordance with the invention, from 0.8 to 1.2 molar equivalents, especially from 0.9 to 1.1 molar equivalents, of formaldehyde and from 0.8 to 1.2 molar equivalents, especially from 0.9 to 1.1 molar equivalents, of hydrocyanic acid are used.

In the case of glutamic acid, preference is given to using its monoalkali metal salt, especially the monosodium salt monohydrate. In contrast, the aspartic acid is preferably used in the form of the free aminodicarboxylic acid. Among the aminodicarboxylic acids of the formula II, the L-isomers or salts thereof are preferred.

The reaction in step a) is effected generally in a solvent. The concentration of the aminodicarboxylic acid or salt thereof is preferably from 10 to 60% by weight and especially from 20 to 50% by weight, based on the total weight of the reaction mixture.

In a preferred embodiment, the reaction is effected in an aqueous solvent. In the process according to the invention, aqueous solvents are understood to mean water or mixtures of water with water-soluble organic solvents. Useful organic solvents here include especially methanol, ethanol, n-propanol, isopropanol, tert-butanol, dioxane or tetrahydrofuran, or mixtures of these organic solvents with one another. The proportion of water-soluble organic solvents will preferably not exceed 50% by volume and especially 20% by volume, based on the total amount of the aqueous solvent.

Preference is given to initially charging the aminodicarboxylic acid II or a salt of II in the reaction vessel, preferably in the desired solvent.

The formaldehyde and hydrocyanic acid reactants can be added simultaneously or successively. In a preferred embodiment, first the formaldehyde and then the hydrocyanic acid is added to the aminodicarboxylic acid of the formula II or salt thereof. This is understood to mean that the majority, especially at least 80%, of the formaldehyde is added to the reaction vessel before the hydrocyanic acid is added. It is also preferred to add the two reactants in each case over relatively short periods of from about 10 seconds up to 1 hour, more particularly depending especially on the evolution of temperature or other factors, for example the batch size. After the addition has ended, the mixture is generally allowed to continue to react, for example over a period of from about 1 minute up to 5 hours, especially until no exothermicity can be detected any longer.

The reactions of step a) are effected preferably under temperature control and typically at temperatures in the range from 0 to 100° C., especially from 10 to 70° C. In a preferred embodiment, there is neither external heating nor external cooling during the reactions.

It is assumed that, in step a), the main component formed is the aminodicarboxylic acid N-monoacetonitrile. The secondary components which occur may be the aminodicarboxylic acid used as the reactant, the aminodicarboxylic acid N,N-diacetonitrile, and hydrolysis products of the acetonitrile compounds mentioned, for example corresponding amides and partial amides, and also the salts of the aforementioned compounds.

The reaction product of step a) can be used in step b) of the process according to the invention either with or without preceding workup. For workup, it is possible to use processes familiar to those skilled in the art for removing the solvent and optionally for purifying the product, for example concentrating to dryness, spray- or freeze-drying, precipitation and crystallization. Preference is given, however, to not performing any workup, and to effecting the reactions which follow according to step b) directly in the reaction mixture obtained in step a).

In step b), the reaction product obtained from step a) is reacted with, based on the compound of the formula II used, from 0.8 to 1.2 molar equivalents, especially from 0.9 to 1.1 molar equivalents, of hydrocyanic acid, and with from 0.8 to 1.2 molar equivalents, especially from 0.9 to 1.1 molar equivalents, of formaldehyde.

The reaction in step b) is effected typically by adding the hydrocyanic acid and the formaldehyde to the reaction product obtained in step a). In a preferred embodiment, the hydrocyanic acid and formaldehyde reactants are added directly to the reaction mixture which has been obtained in step a). If the solvent has been partly or fully removed after step a), preference is given to taking the mixture up in an aqueous solvent beforehand.

The hydrocyanic acid and formaldehyde reactants can be added in step b) simultaneously or successively to the reaction mixture obtained in step a). In a preferred embodiment, first the hydrocyanic acid and then the formaldehyde is added. This is understood to mean that the majority, especially at least 80%, of the hydrocyanic acid is added to the reaction vessel before the formaldehyde is added.

In another embodiment of the invention, in step b), the hydrocyanic acid and the formaldehyde are added in parallel, i.e. the majority, i.e. at least 50% and especially at least 80%, of the formaldehyde and of the hydrocyanic acid are added within the same period.

It is also preferred to add the two reactants each over relatively short periods of from about 10 seconds up to 1 hour, depending especially on the evolution of temperature or other factors, for example the batch size.

After the addition has ended, the mixture is generally allowed to continue to react, for example over a period of from about 1 minute up to 5 hours, especially until no exothermicity is detectable any longer.

The reactions of step b) are effected preferably under temperature control and typically at temperatures of from 0 to 100° C., especially from 20 to 90° C. In a preferred embodiment, there is neither external heating nor external cooling during the reactions.

For the reactions of steps a) and b), a wide pH range is generally suitable. Typically, reactions with hydrocyanic acid are performed at pH values in the range from pH 0 to pH 12, especially from pH 1 to pH 10. Preference is given to allowing the reactions to proceed under autogenous pH, and no measures are taken to adjust the pH before or during the reactions.

The reaction product of step b) can be used in step c) of the process according to the invention either with or without preceding workup. For the workup, it is possible to use processes familiar to those skilled in the art for removing the solvent and optionally for drying the product, for example concentration to dryness, spray- or freeze-drying, precipitation and crystallization. However, preference is given to performing no workup and to effecting the reactions which follow in step c) directly with the reaction mixture obtained in step b).

In step c), the reaction product obtained from step b) is hydrolyzed under acidic or preferably basic conditions, in order to convert nitrile groups present and amide groups optionally present to carboxyl groups. In general, step c) is performed under temperature control and, in accordance with preferred embodiments, either without or, during the contacting of the reaction product from step b) with the base or acid, with external cooling.

The acidic hydrolysis is effected preferably with aqueous hydrochloric acid or aqueous sulfuric acid. Typically, the acid is added, especially depending on the evolution of temperature, within a period of from 10 minutes to 10 hours and especially from 30 minutes to 3 hours, to the aqueous reaction mixture obtained in step b). If the solvent has been removed after step b), the mixture is generally taken up in an aqueous solvent beforehand. The temperatures during the addition are typically from 10 to 100° C., especially from 20 to 80° C.

For the basic hydrolysis, preference is given to using aqueous solutions of potassium hydroxide and especially sodium hydroxide, in concentrations of from 5 to 50% by weight and especially from 20 to 50% by weight. Typically, the aqueous reaction mixture obtained in step b), more particularly depending on the evolution of temperature, is added within a period of from 10 minutes to 10 hours and especially from 30 minutes to 3 hours directly to the potassium hydroxide or sodium hydroxide solution. If the solvent has been removed after step b), the mixture is generally taken up in an aqueous solvent beforehand. The temperatures during the addition are typically from 10 to 100° C., especially from 20 to 80° C.

After the reaction product from step b) has been contacted with base or acid, the mixture is generally heated to from 60 to 120° C., especially to from 95 to 110° C., over a period of from about 10 minutes to up to 10 hours to complete the hydrolysis, preferably until the evolution of ammonia has ended.

The molar equivalents of sodium hydroxide typically used in the hydrolysis for the preparation of the tetrasodium salt of aminodicarboxylic acid-N,N-diacetic acid, based on the compound II used in step a), can be determined by the following formula:

molar equivalents of NaOH=((4 to 4.1)−Y)

where Y is the number of carboxylate groups of the compound II. When the starting material is, for example, the monosodium salt of the aminodicarboxylic acid, from 3.0 to 3.1 molar equivalents of sodium hydroxide are accordingly required for the hydrolysis. Analogously, the monosodium tripotassium salt can be obtained in the reaction with about the same number of molar equivalents of potassium hydroxide. The conditions needed for the preparation of compounds I with other cation combinations can be determined easily by the person skilled in the art.

Alternatively, the compounds II, before they are converted in step a), can be neutralized fully or partly from 0 to 100% in the case of the monoalkali metal salts and from 0 to 200% in the case of the free dicarboxylic acids. Such a neutralization is effected generally with sodium or potassium base. The molar equivalents of alkali metal hydroxide (MOH) which are then typically required for the basic hydrolysis in step c) are calculated as follows:

molar equivalents of MOH=((4 to 4.1)−Y−Z/100)

where Y corresponds to the above definition and Z is the degree of neutralization in the range from 0 to 100% when Y=1, or from 0 to 200% when Y=0. When, for example, the abovementioned monosodium salt of the compound II is partly neutralized to an extent of 25%, this formula gives an amount of from 2.75 to 2.85 molar equivalents of MOH which should be used to prepare the tetraalkali metal salt in step c). The same result is obtained for the case that the free dicarboxylic acid of the compound II is used partly neutralized to an extent of 125%.

In accordance with a further embodiment of the invention, the product obtained in case of acidic hydrolysis can be neutralized with a sodium or potassium base, for example NaOH, KOH, Na$_2$CO$_3$, K$_2$CO$_3$, NaHCO$_3$ or KHCO$_3$, and the desired aminodicarboxylic acid-N,N-diacetic acid salt can be obtained in this way. As is immediately evident to the person skilled in the art, it is also possible to prepare the mono-, di- and trialkali metal salts through the use of suitable amounts of base. In addition, the different mixed sodium-potassium salts can be obtained through corresponding combinations of sodium and potassium bases.

The process according to the invention can be carried out in a batchwise process, a semibatchwise process or in a continuous process. In the case of continuous performance, in step a), for example, a compound II and formaldehyde can be metered in in parallel in a first reaction zone, and then hydrocyanic acid can be metered in in a second reaction zone. Step b) can be performed, for example, in an analogous manner, in which case the reaction mixture from step a) and the hydrocyanic acid are first fed in in parallel, and then, in a further reaction zone, the formaldehyde is fed in. Alternatively, all three components of this step can be combined in parallel in one reaction zone. For the basic hydrolysis, for example, the reaction mixture thus obtained can be metered in in parallel with sodium hydroxide solution in a further reaction zone. Proceeding from this, the person skilled in the art can easily develop corresponding semibatchwise processes. For the process according to the invention, preference is given to employing a semibatch process in which steps a) and b) are performed in a batch reactor, preferably as a one-pot reaction, and step c) preferably in a 2nd batch reactor with metered addition of the solution b) to the initially charged alkali metal hydroxide solution. For further details, reference is made to the example of the application.

After the hydrolysis, the reaction mixture obtained can be sent directly to an industrial use. For instance, an about 38 to 40% by weight aqueous solution of the tetrasodium salt of the compound I constitutes a common saleable product. Alternatively, the compound I can be isolated from the reaction mixture of the hydrolysis and worked up. For this purpose, processes known to those skilled in the art are available, especially for removing the solvent and optionally for purification, for example concentration to dryness, spray- or freeze-drying, precipitation and crystallization. Typically, the compound I is obtained directly from the reaction mixture by removing the solvent, preferably by spray-drying.

The process according to the invention affords the compounds of the formula I in high yields of generally more than 88%, especially more than 92%, based on the compound of the formula II used. The process according to the invention affords the compounds of the formula I in high purity. The NTA content is generally below 0.75% by weight and especially below 0.25% by weight, based on 100% of the compound I.

Optionally, further steps for workup and finishing which are known to those skilled in the art may follow, for example precipitation, crystallization and double decomposition.

Another possibility might be a step for bleaching the aqueous solution, for example by treatment with activated carbon or by oxidation by means of hydrogen peroxide or UV induction.

The invention further provides salts of glutamic acid-N,N-diacetic acid comprising less than 0.75% by weight, especially comprising less than 0.25% by weight, of salts of NTA, based on 100% of the compound I. Salts with these characteristics can be provided with the aid of the process according to the invention.

The examples which follow serve to illustrate the invention:

EXAMPLE

Preparation of L-Glutamic Acid-N,N-Diacetic Acid Tetrasodium Salt

A reaction vessel was initially charged with an approx. 40% by weight solution of 187 g (1.0 mol) of L-glutamic acid monosodium salt monohydrate in 280.5 g of water. To this were added with stirring and without cooling first, within 30 seconds, 100.0 g (1.0 mol) of a 30% by weight aqueous formaldehyde solution and then, within 40 seconds, 27.0 g (1.0 mol) of hydrocyanic acid at ambient temperature. After the addition had ended, the mixture was stirred for a further 5 minutes. Thereafter, no further evolution of heat was detectable and the temperature was 45° C. The resulting mixture was then admixed with stirring and without cooling first, within 70 seconds, with 27.0 g (1.0 mol) of hydrocyanic acid and then, within 160 seconds, with 100.0 g (1.0 mol) of a 30% by weight aqueous formaldehyde solution, in the course of which the temperature rose to about 60° C. After the addition had ended, the mixture was stirred for another about 5 minutes. The resulting about 720 g of a pale yellowish solution were then metered into 489.6 g (3.06 mol) of a 25% by weight sodium hydroxide solution at 25° C. within 1 hour. After the addition had ended, the temperature was 60° C. The mixture was subsequently heated to from 100 to 110° C. until, after about 4 hours, no further evolution of ammonia was detectable. 1100 g of a yellow solution were obtained which, according to HPLC analysis, comprised 330 g of the L-glutamic acid-N,N-diacetic acid tetrasodium salt and hence constituted an about 30% by weight solution of the product. Based on the glutamate used, a yield of 94% was obtained. The proportion of NTA trisodium salt in the solution, determined by means of HPLC, was 0.05% by weight.

COMPARATIVE EXAMPLE

Preparation of L-glutamic acid-N,N-diacetic acid tetrasodium salt (performance analogous to examples 1 and 2 of DE 4211713, except using the monosodium salt of glutamic acid instead of aspartic acid)

A reaction vessel was initially charged with a solution of 187 g (1.0 mol) of L-glutamic acid monosodium salt monohydrate in 300.0 g of water. To this were added simultaneously with stirring 200 g (2.0 mol) of a 30% by weight aqueous formaldehyde solution and 54.0 g (2.0 mol) of hydrocyanic acid within 1 hour, in the course of which the temperature was kept at from 20 to 25° C. by cooling. After the addition had ended, the mixture was heated to 70° C. over a period of 1 hour. The resulting reaction mixture was then added dropwise to 408.0 g (3.06 mol) of a 30% by weight sodium hydroxide solution at 40° C. within 1 hour. After the addition had ended, the mixture was heated to 100° C. until, after about 4 hours, no further evolution of ammonia was detectable. 1041 g of a solution were obtained which, according to HPLC analysis, comprised 312.4 g of L-glutamic acid-N,N-diacetic acid tetrasodium salt and hence constituted an about 30% by weight solution of the product. Based on glutamate used, a yield of 89% was obtained. The proportion of NTA trisodium salt in the solution, determined by means of HPLC, was 0.35% by weight.

The invention claimed is:

1. A process for preparing aminodicarboxylic acid-N,N-diacetic acids of formula (I):

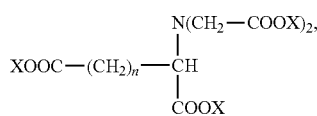
(I)

in which X is independently hydrogen or alkali metal, and n is 1 or 2, the process comprising:
a) reacting an aminodicarboxylic acid of formula (II):

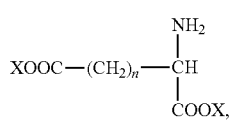
(II)

with from 0.8 to 1.2 molar equivalents of formaldehyde and with from 0.8 to 1.2 molar equivalents of hydrocyanic acid, by adding formaldehyde and hydrocyanic acid, wherein the aminodicarboxylic acid is initially charged in the reaction vessel and then formaldehyde and hydrocyanic acid are added, to yield a first reaction product, wherein after completion of the addition the reaction was allowed to continue until no further evolution of heat is detectable;

b) further reacting the first reaction product obtained in a) with from 0.8 to 1.2 molar equivalents of hydrocyanic acid, and with from 0.8 to 1.2 molar equivalents of formaldehyde to yield a second reaction product;

c) hydrolyzing the second reaction product obtained in b).

2. The process according to claim 1, wherein, in a), first the formaldehyde and then the hydrocyanic acid is added to the aminodicarboxylic acid of formula (II).

3. The process according to claim 1, wherein, in b), the formaldehyde is added after the hydrocyanic acid has been added.

4. The process according to claim 1, wherein, in b), the further reacting is effected by parallel addition of formaldehyde and hydrocyanic acid.

5. The process according to claim 1, wherein the reacting in a) is carried out in an aqueous solvent.

6. The process according to claim 1, wherein the further reacting in b) is effected without preceding workup of the first reaction product obtained in a).

7. The process according to claim 1, wherein the hydrolyzing in c) is effected without preceding workup of the second reaction product obtained in b).

8. The process according to claim 1, wherein the hydrolyzing in c) is effected under basic conditions.

9. The process according to claim 8, wherein the hydrolyzing is effected with aqueous sodium hydroxide solution.

10. The process according to claim 1, wherein, in a) and b), from 0.9 to 1.1 molar equivalents each of formaldehyde and hydrocyanic acid are added.

11. The process according to claim 1, wherein n is 2.

12. The process according to claim 11, wherein, in a), L-glutamic acid monosodium salt is the aminodicarboxylic acid of formula (II).

13. The process according to claim 1, which is performed continuously.

14. The process according to claim 1, which is performed batchwise.

15. The process according to claim 14, which is performed semibatchwise.

16. The process according to claim 2, wherein, in b), the formaldehyde is added after the hydrocyanic acid has been added.

17. The process according to claim 2, wherein, in b), the further reacting is effected by parallel addition of formaldehyde and hydrocyanic acid.

18. The process according to claim 2, wherein the reacting in a) is carried out in an aqueous solvent.

* * * * *